United States Patent [19]

Bartmann et al.

[11]  4,282,222

[45]  Aug. 4, 1981

[54] 3-PIPERIDINO OR APIPERAZINO-1-PHENYL OR 1-SUBSTITUTED PHENYL ISOQUINOLINE AND ANTIDEPRESSANT COMPOSITIONS THEREOF

[75] Inventors: Wilhelm Bartmann; Elmar Konz, both of Bad Soden am Taunus, Fed. Rep. of Germany; Harry M. Geyer, Somerville, N.J.

[73] Assignee: Hoechst Aktiengesellschaft, Frankfurt am Main, Fed. Rep. of Germany

[21] Appl. No.: 75,038

[22] Filed: Sep. 12, 1979

Related U.S. Application Data

[63] Continuation-in-part of Ser. No. 033,325, Apr. 25, 1979, abandoned.

[30] Foreign Application Priority Data

Apr. 27, 1978 [DE]  Fed. Rep. of Germany ....... 2818403

[51] Int. Cl.$^3$ ................... A61K 31/47; A61K 31/495; C07D 401/04
[52] U.S. Cl. ................................ 424/250; 260/244.4; 424/248.4; 424/258; 544/128; 544/363; 546/90; 546/143
[58] Field of Search ................ 544/363, 128; 546/143, 546/90; 424/250, 258; 260/244.4

[56] References Cited

U.S. PATENT DOCUMENTS 3,517,005  6/1970  Cronin et al. ................ 546/143
3,975,524  8/1976  Nickl et al. .................. 544/58

Primary Examiner—Paul M. Coughlan, Jr.
Attorney, Agent, or Firm—Curtis, Morris & Safford

[57]  ABSTRACT

Isoquinolines of the formula

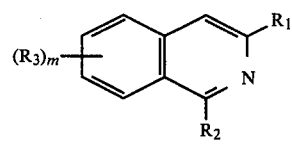

in which $R_1$ is piperidino, piperazino or piperazino N-substituted thereof by alkyl of 1 to 4 carbon atoms, alkylene of 1 to 4 carbon atoms wherein said alkylene is substituted in turn by fluorobenzoyl, or CHO; $R_2$ is phenyl or phenyl substituted by alkyl of 1 to 4 carbon atoms, halogen, amino or nitro; and $R_3$ is hydrogen or halogen, a process for their preparation and medicaments containing the isoquinolines, especially the use of said medicaments as antidepressants.

5 Claims, No Drawings

3-PIPERIDINO OR APIPERAZINO-1-PHENYL OR 1-SUBSTITUTED PHENYL ISOQUINOLINE AND ANTIDEPRESSANT COMPOSITIONS THEREOF

This application is a continuation-in-part application of U.S. patent application Ser. No. 0,33,325, filed Apr. 25, 1979, now abandoned.

The present invention relates to novel isoquinoline derivatives and to a process for their preparation.

3-Amino-4-phenyl-isoquinoline derivatives acting on the central nervous system and 3-piperazinoisoquinolines having a strong inhibitory effect on thrombocyte aggregation have been described in German Offenlegungsschriften Nos. 2,030,675 and 2,503,961, respectively.

There have now been found isoquinolines carrying substituents in the 3-position, which compounds have valuable pharmacological, especially psychotropic properties.

The present invention therefore provides isoquinolines of the general formula I.

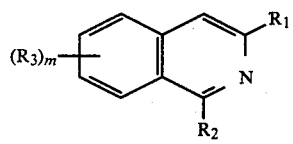

in which
m is 1 or 2,
$R_1$ is an amino group of the formula

in which $R_4$ and $R_5$ which are identical or different stand for hydrogen or a straight-chain or branched saturated or unsaturated alkyl radical of from 1 to 8 carbon atoms, the alkyl radicals optionally being substituted by hydroxy, $C_1$–$C_4$-alkoxy or an amino group of the formula

in which $R_6$ and $R_7$ are identical or different and represent hydrogen or a straight-chain or branched alkyl radical of from 1 to 6 carbon atoms, or together with the nitrogen atom represent a heterocyclic ring of up to 7 carbon atoms. The alkyl radicals $R_4$ and $R_5$ may also form a 5- to 8-membered ring together with the nitrogen atom, wherein one carbon atom of the heterocyclic ring may be substituted by $C_1$–$C_6$-alkyl, $C_1$–$C_4$-alkoxy, hydroxy, carboxy, or $C_1$–$C_4$-alkoxycarbonyl and in which one of the carbon atoms may be replaced by an oxygen, sulfur or nitrogen atom, which latter is optionally substituted by hydrogen, thienyl, furyl, pyridyl or formyl, $C_3$–$C_8$-alkenyloxycarbonyl or $C_3$–$C_8$-alkinyloxycarbonyl, $C_1$–$C_6$-alkoxycarbonyl optionally substituted by hydroxy or $C_1$–$C_4$-alkoxy groups, a phenyl radical which may carry one or several substituents, such as $C_1$–$C_4$-alkyl, $C_1$–$C_4$-alkoxy, methylenedioxy, hydroxy, nitro or amino, or halogen, and in which the hydrogen atom at the nitrogen atom may further be replaced by the radical —$COR_8$, wherein $R_8$ represents thienyl, furyl, pyridyl or a phenyl radical optionally being substituted as above, or $C_1$–$C_6$-alkyl optionally being substituted in its turn by hydroxy, $C_1$–$C_4$-alkoxy, $C_1$–$C_6$-dialkylamino, ethylene-dioxy, trimethylene-dioxy or a phenyl radical optionally being substituted as above;

$R_2$ is a phenyl radical optionally being mono- or di-substituted by halogen, hydroxy, nitro, amino or amino being substituted by one or two aliphatic, cycloaliphatic or aromatic hydrocarbon radicals and having from 2 to 18 carbon atoms, the nitrogen atom optionally being included in a heterocyclic ring, by acylamino, alkyl or alkoxy with 1 to 6 carbon atoms each, by benzyloxy or trifluoromethyl, or is a pyridyl or thienyl radical;

$R_3$ is hydrogen, halogen, hydroxy, alkyl or alkoxy with 1 to 6 carbon atoms, nitro, amino, benzyloxy, methylenedioxy or ethylene-dioxy, and the physiologically acceptable salts thereof, a process for the preparation of the compounds, pharmaceutical compositions, and the use of said compounds.

The invention relates in particular to compounds in which $R_1$ is an amino group of the formula

wherein $R_4$ and $R_5$ are identical or different and represent hydrogen, a straight-chain or branched saturated or unsaturated alkyl radical of from 1 to 4 carbon atoms, said alkyl radicals optionally forming-together with the nitrogen atom-a 5- to 7-membered ring in which one of the carbon atoms may be replaced by an oxygen, sulfur or nitrogen atom, which latter may be substituted by hydrogen, thienyl, furyl, pyridyl or formyl, $C_1$–$C_4$-alkoxycarbonyl optionally being substituted by hydroxy or $C_1$–$C_4$-alkoxy, the phenyl radical which may carry one or several substituents, such as $C_1$–$C_4$-alkyl, $C_1$–$C_4$-alkyl, $C_1$–$C_4$-alkoxy, methylene-dioxy, hydroxy, nitro or amino, or halogen, and in which the hydrogen atom at the nitrogen atom may further be replaced by the radical —$COR_8$, wherein $R_8$ represents thienyl, furyl, pyridyl, or a phenyl radical optionally substituted as above, or $C_1$–$C_4$-alkyl optionally being substituted in its turn by hydroxy, $C_1$–$C_4$-alkoxy, $C_1$–$C_4$-dialkylamino or the phenyl radical optionally substituted as above, and in which—if $R_4$ represents hydrogen or $C_1$–$C_4$-alkyl-$R_5$ is an aminoalkyl radical of the formula

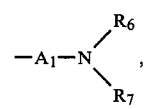

in which $R_6$ and $R_7$ are defined as above and $A_1$ represents a straight-chain or branched $C_2$–$C_6$-alkylene group which may be substituted by hydroxy or $C_1$–$C_4$-alkoxy groups.

The preferred substituents for $R_2$ represent a phenyl ring optionally mono- or disubstituted by halogen, nitro, alkyl or alkoxy groups of from 1 to 4 carbon atoms, or amino groups, and $R_3$ stands for hydrogen, halogen, hydroxy, nitro, amino, alkyl or alkoxy of from 1 to 4 carbon atoms.

Of particular interest are those compounds in which $R_1$ represents an amino radical of the formula $$-N\begin{matrix}R_4\\ \\R_5\end{matrix}$$

in which the alkyl radicals $R_4$ and $R_5$ together with the nitrogen atom form a 5- to 7-membered ring and in which one of the carbon atoms may be replaced by a N- or O-atom, especially the pyrrolidino, piperidino, hexamethyleneimino, morpholino, 4-hydroxypiperidino, 4-carbethoxypiperidino and the 1-piperazinyl radical $$-N\underbrace{\phantom{XXXX}}N-X,$$

in which X is hydrogen, $C_1$–$C_4$-alkyl, $\beta$-hydroxyethyl, 3,4-methylenedioxybenzyl, phenyl, phenyl substituted by methoxy, chlorine, nitro or amino, 3,4,5-trimethoxybenzoyl, 3,4-methylene-dioxybenzyl, 2-furoyl, 2-thienyl, $C_1$–$C_3$-alkoxycarbonyl, the alkyl radical in the latter optionally being substituted by OH or methoxy and ethoxy, or—if $R_4$ represents hydrogen or $C_1$–$C_4$-alkyl, $R_5$ is an aminoalkyl radical of the formula $$-A_1-N\begin{matrix}R_6\\ \\R_7\end{matrix}$$

in which $A_1$, $R_6$ and $R_7$ are defined as above. An especially important substituent for $R_2$ is the phenyl radical optionally mono- or disubstituted by halogen, hydroxy, nitro, amino or methoxy groups, and for $R_3$ there are to be mentioned hydrogen, halogen, hydroxy or methoxy groups, preferably in the 6- and/or 7-positions. Another subject of the invention are processes for the preparation and pharmaceutical compositions of the said compounds.

The process for preparing the compounds of formula I comprises (a) reacting compounds of the formula II $$(R_3)_m\text{—}\underset{R_2}{\text{[isoquinoline ring]}}\overset{CO_2H}{\underset{Y}{}}\quad\text{II}$$

in which Y is chlorine or bromine and $R_2$, $R_3$ and m are defined as in formula I, with an amine of the formula $$H-N\begin{matrix}R_4\\ \\R_5\end{matrix}$$

in which $R_4$ and $R_5$ are defined as in formula I above;
(b) reacting compounds of the formula III $$(R_2)_m\text{—}\underset{R_2}{\text{[isoquinoline ring]}}\text{—}Y\quad\text{III}$$

in which Y is chlorine or bromine and $R_2$, $R_3$ and m are defined as above in formula II, with an amine of the formula $$H-N\begin{matrix}R_4\\ \\R_5\end{matrix}$$

in which $R_4$ and $R_5$ are defined as in formula I above;
(c) reacting compounds of the formula IV $$(R_3)_m\text{—}\underset{R_2}{\text{[isoquinoline ring]}}\text{—}R_1\quad\text{IV}$$

in which $R_1$, $R_2$, $R_3$ and m are defined as in formula I with the proviso that the radical $R_1$ contains a secondary amino group, with an alkylating agent of the formula $Z-R_9$, in which Z represents iodine, chlorine or bromine, and $R_9$ is a straight-chain or branched $C_1$–$C_6$-alkyl radical optionally being substituted by hydroxy, $C_1$–$C_4$-alkoxy, $C_1$–$C_4$-dialkylamino, ethylene-dioxy, trimethylene-dioxy or the group $$CO-N\begin{matrix}R_6\\ \\R_7\end{matrix}$$

in which $R_6$ and $R_7$ are defined as in formula I, or by optionally substituted phenyl, or is a $C_3$–$C_8$-alkenyl or $C_3$–$C_8$-alkinyl radical, or with a chloroformic acid ester of the formula Cl—$CO_2$ ($C_1$–$C_4$)-alkyl, the alkyl radicals carrying hydroxy or $C_1$–$C_4$-alkoxy groups, or with a compound of the formula Cl—$COR_8$, in which $R_8$ is defined as in formula I above;

(d) substituting the phenyl ring in compounds of the formula I $$(R_3)_m\text{—}\underset{R_2}{\text{[isoquinoline ring]}}\text{—}R_1\quad\text{I}$$

in which $R_1$, $R_3$ and m are defined as in formula I above and $R_2$ represents the phenyl ring, in a second reaction step;

(e) modifying a radical $R_3$ or any substituents which may be present at the phenyl ring in the 1-position in a way that further compounds of the general formula I are formed.

In process variant (a) at least twice the equivalent amount of amine is added, as 1 mol of amine is used for the formation of the hydrogen halide split off, however, sometimes it is advantageous to employ the amine in an excess amount of up to 15 times, in order to accelerate the reaction. If the reaction is carried out with equimolar amounts of amine, tertiary amines, such as picoline, 1,4-diazabicyclo-(2,2,2)-octane, 1,5-diazabicyclo[5,4,0]undec-5-ene or potassium carbonate may be added as acid-binding agents. As far as solvents are used for the reaction, there may be mentioned indifferent, anhydrous, organic solvents, such as ethylene-glycol-monoethyl ether, octanol, diethylene-glycol-dimethyl ether, diethylene-glycol-dibutyl ether, toluene, xylene, chlorobenzene, dichlorobenzene, trichlorobenzene, dimethylformamide, dimethylsulfoxide, or hexamethyl-phosphoric acid triamide. The reaction is generally carried out at a temperature in the range of from 80° to 220° C., preferably from 120° to 180° C. until the formation of carbon dioxide has been completed. The starting compounds II for process (a) may be obtained according to German Offenlegungsschrift No. 28 11 361, for example, by reacting compounds of the formula V

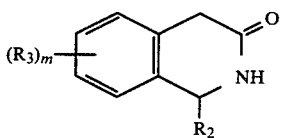

in which $R_2$, $R_3$ and m are defined as in formula I above, with a Vilsmeier addition product of an acid amide with an acid chloride or bromide to give compounds of the formula VI

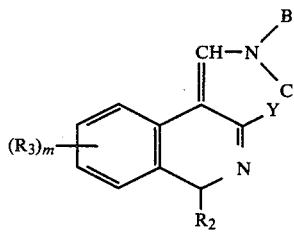

in which Y is chlorine or bromine and B and C represent alkyl or cycloalkyl of 1 to 6 carbon atoms or phenyl, and subsequent oxidation to give compounds of the formula VII

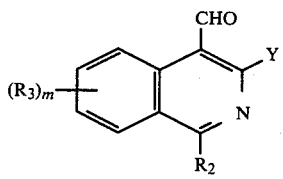

in which Y is chlorine or bromine and $R_2$, $R_3$ and m are defined as in formula I above. A subsequent oxidation of the formyl group to form the carboxyl group yields compounds of the formula II.

In process variant (b) the compounds of the formula II are reacted with an amine in the same manner as in process (a). The starting compounds III for the process (b) may be obtained by reacting compounds VIII

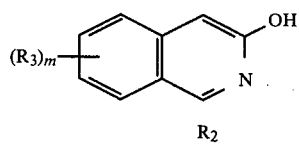

in which $R_2$, $R_3$ and m are defined as in formula I above, with an acid chloride or bromide, such as thionyl chloride, phosphoroxychloride, phosphorus trichloride, phosphorus pentachloride or phosphorus tribromide. Compounds VIII may be prepared in accordance with prescriptions known from literature, for example, by cyclization of o-acylphenyl-acetic acids with ammonia (cf., for example, Khim, Geterotsikl. Soedin. 1976, 8, 1103 and Rocz. chem. 51 (1977) 4, 691).

According to process variant (c) secondary amino groups are alkylated according to known methods with the alkylating agent Z—$R_9$.

According to process variant (d) substituents may be introduced in the aromatic radical $R_2$ by way of electrophilic substitution. This includes above all the halogenation, sulfonation or nitration processes, the nitration being of particular interest. The process is carried out by subjecting compounds of the formula I to the common nitration conditions (sulfuric acid, nitric acid, cooling with ice).

According to process variant (e) the substituents $R_3$, which have been subsequently introduced at the radical $R_2$ or which have already been present, may be modified at a later stage, for example a nitro group by reduction, an amino group by alkylation or a methoxy group by ether cleavage, so that further compounds of formula I are formed. Some examples of the great number of possible reactions are to illustrate this fact. By reducing an aromatic nitro group an amino compound is obtained, for example, if $R_2$ represents the 4-nitrophenyl radical, the corresponding 4-aminophenyl compound is formed. This reduction is carried out in usual manner, for example, with Raney-Nickel in ethanol or with iron powder in a hydrochloric solution. A further example is the acylation of an amino group. Thus, for example, if $R_2$ represents the 4-aminophenyl radical, it may be converted into the 4-acetyl-aminophenyl radical under the common conditions, for example with acetanhydride in pyridine, at low temperature (from 0° to 10° C.). The diazotization of an aromatic amino group with subsequent reaction with a nucleophilic group represents another possibility to modify substituents that are already present. For example, if a radical $R_2$ represents the 4-aminophenyl group, it may be converted with nitrous acid (commonly prepared from sodium nitrite and sulfuric acid) at a low temperature (0° to 5° C.) into the corresponding diazonium salt which then yields for example with hydrochloric acid in the presence of copper chloride the 4-chlorophenyl radical, or by concentration the 4-hydroxyphenyl group. The cleavage of an alkoxy group to yield the corresponding hydroxy compound also represents a method for converting the various substituents. Thus, for example, the ether cleavage of a 7-methoxy compound ($R_3$=$OCH_3$) with hydrogen bromide in aqueous acetic acid at a temperature of from 50° to 120° C. yields the corresponding 7-hydroxy compound. The oxidation of a methyl group to give the carboxy group or the reduction of an aldoxime group to yield an amino group may be mentioned as additional examples.

The claimed isoquinolines are useful antidepressants. It has been shown that they are more potent than any standard compounds in the tests predictive of antidepressant activity, eg. tetrabenazine and reserpine antagonism. This activity was supported in biochemical tests of amine uptake-inhibition which indicated that they are at least equal to desipramine in inhibiting neuronal noradrenaline uptake without monoamineoxidase inhibition both in vitro and in vivo. However, they are almost inactive in inhibiting dopamine uptake and this correlates well with their inability to produce any motor stimulation or stereotypic behavior.

Moreover, the claimed isoquinolines have an unusual activity for an antidepressant as they inhibit methamphetamine toxicity in aggregated mice. They apparently are free of anticholinergic effects and produce no overt sedation or potentiation of hexobarbital sedation. In cardiovascular experiments they are extremly potent in potentiating noradrenaline and inhibiting tyramine effects while apparently less cardio-toxic than imipramine. In mice, they have less than one-half the acute toxicity of standard antidepressants and at least twice the potency.

The dosage required to treat a human patient suffering from depressions depends on the nature and the extent of the depression. Generally, small dosages will be administered initially with gradual increase in dosage until the optimum dosage level is determined for the particular patient under treatment. It will generally be found that when the composition is administered orally, larger quantities of the active ingredient will be required to produce the same antidepressive effect as would be produced by the smaller quantity of the active compound which is administered parenterally. In general, dosages will be in the range from about 5 to 50 mg/kg per day if administered orally, whereas dosages of from 1 to 30 mg/kg per day are used for intravenous administration.

The novel compounds may be used either by themselves or in conjunction with physiologically acceptable auxiliary agents or carriers. For oral administration the active compounds are mixed with the substances common for this purpose and are brought by usual methods into suitable dosage unit forms, such as tablets, gelatin capsules, aqueous, alcoholic or oily suspensions or aqueous alcoholic or oily solutions. As inert carriers there may be used, for example, magnesium carbonate, lactose or corn starch. The composition may be prepared in the form of dry or moist granules. As oily carriers or solvents there may be mentioned in particular vegetable and animal oils, for example sunflower oil or cod-liver oil.

A special way of administration is to be seen in the intravenous application. For this purpose the active compounds or the physiologically acceptable salts thereof are dissolved with the substances common for this process. Physiologically acceptable salts of this kind are formed, for example, with the following acids: Hydrochloric, hydrobromic or hydriodic acid, phosphoric acid, sulfuric acid, methylsulfuric acid, amidosulfonic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicylic acid, hydroxyethane-sulfonic acid, benzene-sulfonic acid, or synthetic resins which contain acid groups, for example those having an ion exchange effect. As solvents of the corresponding physiologically acceptable salts of the active compounds for intravenous application there may be mentioned, for example: Water, physiological salt solutions or alcohols, such as ethanol, propane diol or glycerol, furthermore sugar solutions, for example glucose or mannitol solutions, or a mixture of the various solvents specified above.

The following Examples serve to illustrate the present invention.

EXAMPLE 1

3-N-Methylpiperazino-1-phenyl-isoquinoline

30 Grams of 3-chloro-1-phenyl-isoquinoline-4-carboxylic acid are heated in 90 ml of N-methyl-piperazine within 2 hours to 150° C. The reaction mixture is maintained for 6 hours at 150° C., until the formation of carbon dioxide has been completed. The mixture is cooled, distributed in water and toluene, the toluene phase is washed with water, and after drying the solvent is removed in vacuo. The oily residue is converted with ethanolic hydrochloric acid into the crystalline hydrochloride having a melting point of from 278° to 282° C.

The starting compound 3-chloro-1-phenyl-isoquinoline-4-carboxylic acid is prepared as follows:

53.5 Grams of 3-chloro-1-phenyl-isoquinoline-4-aldehyde are suspended in 1.5 l of acetone and 500 ml of phosphate buffer of pH 7. At 40° C., 40 g of potassium permanganate are introduced portionwise within 3 hours, and stirring is continued at the said temperature for another 2 hours. The excess potassium permanganate is destroyed with 10 g of sodium hydrogenosulfite, and the solution is concentrated to 500 ml and filtered. The filtrate is brought to pH 4 with concentrated hydrochloric acid and is thoroughly extracted with acetic ester. After removing the solvent in vacuo there remain 41.1 g of 3-chloro-1-phenyl-isoquinoline-4-carboxylic acid of a melting point of 208° C.

The 3-substituted isoquinolines of the Examples in Table 1 are prepared according to the above-described method from the 3-chloro-1-phenyl-isoquinoline-4-carboxylic acids and the corresponding bases thereof.

TABLE 1

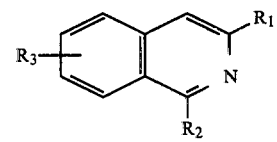

| Example | $R_1$ | $R_2$ | $R_3$ | Melt.p. °C./salt (melt.p. °C.) |
|---|---|---|---|---|
| 2 | —N◯N—CH₃ | —C₆H₅ | 7-Cl | 131–133°/HCl (307–309°) |
| 3 | —N◯N—H | —C₆H₅ | H | 107–118°/HCl (284–287°) |
| 4 | —N◯ | —C₆H₅ | H | oil/HCl (115–157°) |
| 5 | —N◯N—CHO | —C₆H₅ | H | 133–135° |

TABLE 1-continued

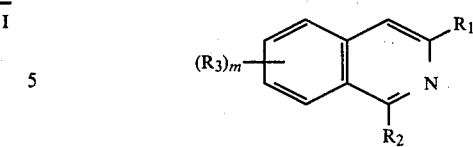

| Example | R₁ | R₂ | R₃ | Melt.p. °C./salt (melt.p. °C.) |
|---|---|---|---|---|
| 6 | −N⌒N−CH₃ | 4-Cl—C₆H₄ | H | /HCl (277–280°) |
| 7 | −N⌒N−CH₃ | 2-CH₃—C₆H₄ | H | resin/HCl (216–218°) |
| 8 | −N⌒N−CH₃ | 2-F—C₆H₄ | H | resin/HCl (146–150°) |
| 9 | −N⌒N−CH₃ | 4-NO₂—C₆H₄ | H | /HCl (287–289°) |

EXAMPLE 10

3-N-Butyl-piperazino-1-phenyl-isoquinoline 6.65 Grams of 3-piperazino-1-phenyl-isoquinoline and 4.73 g of N-butyl bromide are refluxed with 4.88 g of sodium carbonate and 0.2 g of potassium iodide in 150 ml of toluene for 4 days. Upon cooling, the reaction mixture is washed with water, dried and concentrated. There remains a brown oil which together with ethanolic hydrochloric acid yields 5.7 g of crystalline hydrochloride of 3-N-butylpiperazino-1-phenyl-isoquinoline of a melting point of from 216° to 218° C.

EXAMPLE 11

3-N-[3-(4-Fluorobenzoyl)-propyl]-piperazino-1-phenyl-isoquinoline 6.65 Grams of 3-piperazino-1-phenyl-isoquinoline, 6.9 g of -chloro-4-fluorobutyrophenone, 4.88 g of sodium carbonate and 0.2 g of potassium iodide are refluxed in 150 ml of toluene for 5 days. The working up as described in Example 10 yields 8.4 g of a dark resin which crystallizes with ethanolic hydrochloric acid in the form of a hydrochloride having a melting point of from 217° to 220° C.

EXAMPLE 12

3-N-Methylpiperazino-1-(4-aminophenyl)-isoquinoline 4.8 Grams of 3-N-methyl-piperazino-1-(4-nitrophenyl)isoquinoline hydrochloride are hydrogenated in 900 ml of methanol with 1 g of palladium on animal charcoal (10% strength) at room temperature and 1 atmosphere of hydrogen pressure. After 1 hour the theoretical amount of hydrogen has been taken up, the catalyst is filtered off and the solution is concentrated. 3.9 Grams of 3-N-methylpiperazino-1-(4-aminophenyl)-isoquinoline hydrochloride are isolated, the compound having a melting point of from 247° to 248° C.

What is claimed is:

1. An isoquinoline of the formula

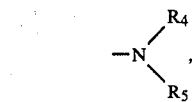

or a physiologically acceptable salt thereof in which m is 1 or 2, $R_1$ is an amino group of the formula

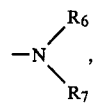

in which $R_4$ and $R_5$, which are identical or different, stand for hydrogen or a straight-chain or branched alkyl of from 1 to 8 carbon atoms, substituted alkyl of 1 to 8 carbon atoms being substituted by hydroxy, $C_1$–$C_4$-alkoxy or an amino group of the formula $$-N\begin{matrix}R_6\\R_7\end{matrix},$$

in which $R_6$ and $R_7$ are identical or different and represent hydrogen or a straightchain or branched alkyl of from 1 to 6 carbon atoms, or together with the nitrogen atom represent a heterocyclic ring of up to 7 carbon atoms; $R_4$ and $R_5$ may also from a 5- to 8-membered heterocyclic ring together with the nitrogen atom, one carbon atom of which may be substituted by $C_1$–$C_6$-alkyl, $C_1$–$C_4$-alkoxy, hydroxy, carboxy, or $C_1$–$C_4$-alkoxycarbonyl and in which one of the carbon atoms of the heterocyclic ring may be replaced by an oxygen, sulfur, nitrogen or nitrogen substituted by thienyl, furyl, pyridyl or formyl, $C_3$–$C_8$-alkenyloxycarbonyl or $C_3$–$C_8$-alkinyloxycarbonyl, $C_1$–$C_6$-alkoxycarbonyl, substituted $C_1$–$C_6$-alkoxycarbonyl substituted by hydroxy or $C_1$–$C_4$-alkoxy, phenyl substituted by one or more $C_1$–$C_4$-alkyl, $C_1$–$C_4$-alkoxy, methylenedioxy, hydroxy, nitro or amino, or halogen, and in which the hydrogen atom at the nitrogen atom in the heterocycle may further be (a) replaced by -COR₈, wherein $R_8$ represents thienyl, furyl, pyridyl, phenyl or phenyl substituted as defined above, or (b) replaced by $C_1$–$C_6$-alkyl substituted in turn by hydroxy, $C_1$–$C_4$-alkoxy, $C_1$–$C_6$-dialkyl-amino, ethylenedioxy, trimethylenedioxy or a phenyl radical; $R_2$ is a pyridyl; thienyl; phenyl or phenyl mono-or disubstituted by halogen, hydroxy, nitro, amino or amino substituted by one or two aliphatic, cycloaliphatic or aromatic hydrocarbon radicals and having from 2 to 18 carbon atoms, by acylamino, by alkyl or by alkoxy, with 1 to 6 carbon atoms each, by benzyloxy or by trifluoromethyl; $R_3$ is hydrogen, halogen, hydroxy, alkyl or alkoxy with 1 to 6 carbon atoms, nitro, amino, benzyloxy, methylene-dioxy or ethylene-dioxy.

2. An isoquinoline of the formula

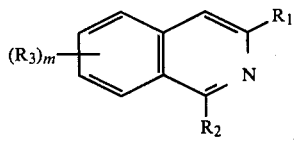

or a physiologically acceptable salt thereof in which m is 1 or 2, $R_1$ is piperidino, piperazino or piperazino N-substituted thereof by alkyl of 1 to 4 carbon atoms, alkylene of 1 to 4 carbon atoms wherein said alkylene is substituted in turn by fluorobenzoyl, or CHO; $R_2$ is phenyl or phenyl monosubstituted by alkyl of 1 to 4 carbon atoms, halogen, amino or nitro; and $R_3$ is hydrogen or halogen.

3. Antidepressant composition comprising an effective amount of a compound as defined in claim 1 and physiologically acceptable auxiliary agent or carrier thereof.

4. A method of treating a human patient having depressions which comprises orally administering to said patient an effective dosage of from about 5 to 500 mg/kg per day of a compound as defined in claim 1.

5. A method of treating a human patient having depressions which comprises intravenously administering to said patient an effective dosage of from about 1 to 30 mg/kg per day of a compound as defined in claim 1.

* * * * *